United States Patent [19]
Burke et al.

[11] Patent Number: 5,296,215
[45] Date of Patent: Mar. 22, 1994

[54] HIGH FOAMING RHEOLOGICALLY STABLE NON-IRRITATING ORAL COMPOSITION

[75] Inventors: Michael R. Burke, Somerset; Michael Prencipe, East Windsor; James M. Buchanan, Mercerville, all of N.J.

[73] Assignee: Colgate-Palmolive Company, Piscataway, N.J.

[21] Appl. No.: 78,527

[22] Filed: Jun. 16, 1993

[51] Int. Cl.$^5$ .................. A61K 7/16; A61K 7/18; A61K 7/22

[52] U.S. Cl. ........................ 424/49; 424/52; 424/54

[58] Field of Search ........................ 424/49-58

[56] References Cited

U.S. PATENT DOCUMENTS

| | | | |
|---|---|---|---|
| 3,696,192 | 10/1972 | Embring | 424/52 |
| 3,954,962 | 5/1976 | Prussin | 424/49 |
| 4,690,776 | 9/1987 | Smigel | 424/49 |
| 4,748,158 | 5/1980 | Biermann et al. | 514/25 |
| 4,920,100 | 4/1990 | Lehmann et al. | 424/49 |
| 4,923,685 | 5/1990 | Wuelknitz et al. | 424/54 |
| 5,041,280 | 8/1991 | Smigel | 424/52 |
| 5,047,177 | 9/1991 | Varco | 252/548 |
| 5,109,127 | 4/1992 | Sekiguchi et al. | 536/115 |
| 5,190,747 | 3/1993 | Sekiguchi et al. | 536/127 |
| 5,200,328 | 4/1993 | Kirk et al. | 536/115 |

*Primary Examiner*—Shep K. Rose
*Attorney, Agent, or Firm*—Paul Shapiro; Robert C. Sullivan

[57] ABSTRACT

An oral composition of acceptable taste substantially non-irritating to oral tissue and stable to viscosity change during storage is disclosed wherein the composition contains a surfactant system comprised of a sodium lauryl sulfoacetate surfactant purified to contain less than 18% by weight impurities and an $C_{12}$–$C_{22}$ alkyl glycoside.

6 Claims, No Drawings

HIGH FOAMING RHEOLOGICALLY STABLE NON-IRRITATING ORAL COMPOSITION

BACKGROUND OF THE INVENTION

1. Field of the Invention

This invention relates generally to a substantially non-irritating oral composition, and more particularly, to a non-irritating oral composition exhibiting high foaming properties and stable rheology.

2. The Prior Art

Sodium lauryl sulfate (SLS) is a widely used surfactant in oral compositions. Surfactants, and particularly anionic surfactants such as sodium lauryl sulfate are an essential ingredient of oral compositions and serve as a solubilizing, dispersing, emulsifying and wetting agent for the other ingredients present in the dentifrice and is especially effective in solubilizing the flavor present. A cosmetic effect of the presence of the surfactant is that it promotes foaming of the oral composition. Oral compositions with strong foaming ability are preferred by consumers since the foaming provides the perception that the oral composition cleans effectively only if it foams well.

The incorporation of anionic surfactants such as sodium lauryl sulfate in oral compositions such as dentifrices is known to cause adverse reactions to oral tissue such adverse reactions being reported in R. C. Caldwell and R. E. Stallard, *A Textbook of Preventive Dentistry*, 196, W. B. Saunders (1977); L. J. Guarnieri, IADR, Abstract No. 661 (1974); L. J. Guarnieri, *Thesis*, University of Indiana (1970). One example is gingival irritation. It is also believed that sodium lauryl sulfate is responsible for sloughing of the oral mucosa.

The art therefore has been seeking a non-irritating alternative to sodium lauryl sulfate as an anionic surfactant for dentifrices.

U.S. Pat. Nos. 4,690,776 and 5,041,280 disclose the use of the anionic surfactant sodium lauryl sulfoacetate in dentifrice formulations. However, the problem of oral irritation due to the presence of anionic surfactants in the dentifrice is not mentioned in the aforesaid patents.

According to the published literature; namely, "Surfactants in Cosmetics (Marcel Dekker), Vol. 16, Ch. 10, Pages 303-304 (1985), sodium lauryl sulfoacetate is of comparatively little importance commercially in oral hygiene products. According to this publication, although the use of sodium lauryl sulfoacetate has been proposed as a foaming agent in dentifrices and other dental preparations, it is not considered as an organoleptically acceptable product for commercial applications.

Attempts to use commercially available sodium lauryl sulfoacetate as a surfactant in oral products such as dentifrices indicate the problem of a bitter taste associated with the presence of the compound in the oral product. Further, compared to sodium lauryl sulfate, dentifrices employing sodium lauryl sulfoacetate as the surfactant exhibit inferior foaming properties. Copending patent application U.S. Ser. No. 07/908,104 Filed Jul. 2, 1992, discloses that dentifrices formulated with a purified form of sodium lauryl sulfoacetate, that is, one having admixed therewith less than 18% non-dodecyl sulfoacetate impurities is organoleptically pleasing when compared to dentifrices formulated with the commercially available unpurified sulfoacetate compound.

Further work in preparing dentifice formulations in which the purified sodium lauryl sulfoacetate is incorporated indicates that on storage in a tube or other similar container the sodium lauryl sulfoacetate forms a lamellar and liquid-crystalline structure with the result that the viscosity of the dentifrice is elevated to a level that the product cannot be readily extruded from the tube or similar container rendering the product unacceptable for consumer use. Attempts to alleviate this viscosity elevation problem by including a nonionic co-surfactant in the dentifrice at a concentration sufficient to provide acceptable rheology has been found to have the disadvantage of imparting either inferior foamability to the dentifrice or an unacceptable bitter taste to the product.

There is therefore a need in the art involving the utilization of purified sodium lauryl sulfoacetate as a surfactant in dentifrices that the problem of unacceptable viscosity change of the stored product be alleviated without deleteriously affecting the foamability or taste of the product.

SUMMARY OF THE INVENTION

In accordance with the present invention, there is provided an oral composition having improved organoleptic properties and rheological storage stability, the oral composition containing a surfactant system comprised of a mixture of purified sodium lauryl sulfoacetate and an alkyl glycoside. The oral composition of the present invention is substantially non-irritating to oral mucosa yet exhibits strong foamability, and has acceptable taste and rheological storage stability.

DESCRIPTION OF THE PREFERRED EMBODIMENTS

The oral compositions of the present invention are formulated using as one of the components of the surfactant system a purified form of sodium lauryl sulfoacetate. The sodium lauryl sulfoacetate material that is commonly commercially available is not the pure compound dodecyl sodium sulfoacetate represented by the formula:

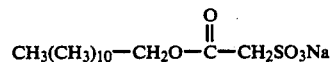

but a mixture of compounds with dodecyl sodium sulfoacetate comprising no more than 70% of the mixture with the remainder being impurities or unreacted products. Thus, as normally employed, the designation or chemical description "sodium lauryl sulfoacetate" to the commercially available product refers to a material containing as impurities, varying amounts of sodium salts of non-dodecyl sodium sulfoacetates; e.g., sodium sulfoacetate, as well as the predominating dodecyl sulfoacetate salt. Commercial sodium lauryl sulfoacetate also contains varying amounts of sodium salts of inorganic acids; e.g., sodium chloride and sodium sulfate, as well as feedstock alcohols; namely, unreacted lauryl alcohol.

Purified sodium lauryl sulfoacetate; i.e. sodium lauryl sulfoacetate having combined therewith 18% or less impurities, hereinafter referred to as "purified sodium lauryl sulfoacetate", is organoleptically more pleasing and has been found to taste better than the unpurified sodium lauryl sulfoacetate.

When used as a component of the surfactant system in the preparation of dentifrices and rinses in accordance with the practice of the present invention, the purified sodium lauryl sulfoacetate material must contain less than about 18% impurities based on the weight of the sodium dodecyl sulfoacetate. A preferred material is a purified sodium lauryl sulfoacetate composition having the following analysis:

| Component | wt % range |
|---|---|
| dodecyl sodium sulfoacetate | 82.0-85.0 min. |
| sodium chloride | 7.5-8.0 max |
| sodium sulfate | 7.5-8.0 max |
| sodium sulfoacetate | <4 max |
| free alcohol | <0.6-0.8 max |

The purified sodium lauryl sulfoacetate is incorporated in the oral compositions of the present invention at a concentration of about 0.1 to about 3.0% by weight and preferably about 0.3 to about 1.5% by weight. At these concentrations, the purified sodium lauryl sulfoacetate is organoleptically acceptable, that is, the normal bitter taste associated with unpurified commercial sodium lauryl sulfoacetate is absent when the purified sulfoacetate is used in oral hygiene products.

Oral compositions prepared using purified sodium lauryl sulfoacetate as the sole surfactant component exhibit inferior foaming properties. The inclusion of an alkyl glycoside in the surfactant systems of oral compositions containing purified sodium lauryl sulfoacetate as the surfactant serves to increase the foamability of the oral composition to levels desired by consumers without deleteriously affecting the organoleptic properties of the oral compositions as well as unexpectedly improving the rheological stability of the dentifrice.

Alkyl glycosides which are incorporated in the oral compositions of the present invention have the formula

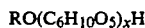

$RO(C_6H_{10}O_5)_xH$ wherein R is an aliphatic residue of a $C_{12-22}$ fatty alcohol and x is an integer from 1 to 20, and preferably 1 to 10 and most preferably 1.2 to 2.0.

Alkyl glycosides are well known to the art. For example, U.S. Pat. No. 4,748,158 discloses the use of alkyl glycosides in combination with antimicrobial biguanide compounds to improve the antimicrobial performance of the antimicrobial compounds. U.S. Pat. No. 4,923,685 discloses an antimicrobial mouthwash containing an antimicrobial biguanide compound, a flavorant and as a surfactant system, a combination of a $C_8$-$C_{14}$ alkyl glycoside and an ethoxylated fatty acid glyceride and sorbitan partial ester.

Alkyl glycosides used in the practice of the present invention are typically produced by reacting glucose or an oligosaccharide with a fatty alcohol containing 12-22 carbon atoms and more preferably with alcohols containing an alkyl group having 12 to 18 carbon atoms. Alkyl glycosides having an alkyl group of 12-16 carbon atoms are preferred in the practice of the present invention. Alkyl glycosides prepared using fatty alcohols containing less than 12 carbon atoms suffer from the presence of lower alkyl chain, e.g., $C_4$-$C_{10}$ free alcohol impurities which deleteriously effect the organoleptic properties of the oral care compositions into which the alkyl polyglycoside is incorporated. Polyglycosides containing $C_{12}$-$C_{16}$ alkyl glycosides are available commercially from Horizon Chemical Division of Henkel, Inc under the trademark "Plantaren".

An especially preferred Plantaren glycoside surfactant is a non-ionic alkyl polyglycoside sold under the trademark Planteren 1200 UP characterized by the formula:

$C_nH_{2n+1}O(C_6H_{10}O_5)_xH$ wherein n=12−16 and X(degree of polymerization)=1.4. The product has a pH of 11.4; a specific gravity at 25° C. of 1.1 gms/ml; a calculated HLB of about 11.5 and a Brookfield viscosity at 35° C., 21 spindle, 5-10 RPM of about 15,000 to about 20,000 centistokes per second.

The alkyl glycoside is incorporated in the oral care compositions of the present invention at a concentration of about 0.1 to about 2.0% by weight and preferably about 0.2 to about 1.0% by weight. In preparing a surfactant system in accordance with the present invention, the purified sodium lauryl sulfoacetate and alkyl glycoside are present in the oral composition at a weight ratio of sulfoacetate to polyglycoside of 10:1 to 1:5, a weight ratio of 3:1 to 1:1 being preferred.

The oral compositions of the present invention may be substantially semi-solid or pasty in character, such as a toothpaste, gel or dental cream. The vehicle of such semi-solid or pasty oral preparations generally contains a polishing material.

Examples of materials useful as polishing agents in the oral composition of the present invention include sodium bicarbonate, water-insoluble siliceous polishing agents, hydrated alumina and dicalcium phosphate, including dicalcium phosphate dihydrate and anhydrous dicalcium phosphate dihydrate and anhydrous dicalcium phosphate. Siliceous polishing agents include colloidal silica xerogel, precipitated silica and sodium aluminiosilicates or silica grades containing combined alumina, typically in amount of about 0.1-7% by weight. Other polishing materials include insoluble sodium metaphosphate, calcium carbonate, trimagnesium phosphate, magnesium carbonate, etc. Mixtures of polishing agents may be used.

Typically, the polishing material is included in semi-solid or pasty dentifrice compositions of the present invention in an amount of from about 15 to about 60% by weight and preferably from about 20 to about 55%.

In toothpaste, gel or dental creams, the oral composition is formulated using a water and humectant carrier typically in an amount ranging from about 10 to about 90% of the composition.

Humectant carriers such as sorbitol, typically commercially available in 70% aqueous solution, glycerine, low molecular weight polyethylene glycol (e.g. about 200 to 600) or propylene glycol exemplify humectant carriers used to formulate the toothpaste, gel or dental compositions and are incorporated in the oral compositions of the present invention at a concentration of about 10 to about 40% by weight and preferably about 15 to about 30% by weight.

Toothpastes, creams and gels typically contain a natural or synthetic thickener or gelling agent in concentrations of about 0.1 to about 10% by weight preferably about 0.5 to about 5 weight %. Suitable thickeners include Irish moss, gum tragacanth, starch, hydroxyethylpropylcellulose, hydroxybutyl methyl cellulose, hydroxypropyl methyl cellulose, hydroxyethyl cellulose and sodium carboxymethyl cellulose.

The oral compositions of the present invention also include products which are substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of the oral compositions of the present invention is generally in the range of from about 6 to about 8.0. The pH can be controlled with acid (e.g., citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain preferred forms of this invention, fluorine-providing salts having anti-caries efficacy may be incorporated in the oral compositions and are characterized by their ability to release fluoride ions in water. Among these materials are inorganic metal salts, for example, sodium fluoride, potassium fluoride, cuprous fluoride, a tin fluoride such as stannous fluoride or stannous chlorofluoride, sodium fluorosilicate, ammonium fluorosilicate, sodium monofluorophosphate, alumina mono-and difluorophosphate.

The amount of the fluoride-providing compound is dependent to some extent upon the type of compound, its solubility, and the type of oral preparation, but it must be a nontoxic amount, generally about 0.01 to about 3.0% in the composition. In a semi-solid or pasty oral composition such as a gel, toothpaste or cream, an amount of such compound may be used, but is preferable to employ sufficient fluoride compound to release about 0.005% to 1%, more preferably about 0.1% of fluoride ion. Typically, in the cases of alkali metal fluorides and stannous fluoride, this component is present in an amount up to about 2.5% by weight, based on the weight of the preparation, and preferably in the range of about 0.05% to 1%. In the case of sodium monofluorophosphate, the compound may be present in an amount of about 0.1–3.0%

In a liquid oral preparation such as a mouthwash or rinse, the fluoride-providing compound is typically present in an amount sufficient to release up to about 1.0%, preferably about 0.001% to 0.5% by weight of fluoride ion. Generally, about 0.01 to about 3.0 wt. % of such compound is present.

Pyrophosphate salts having anti-tartar efficacy such as a dialkali or tetra-alkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate are incorporated in solid oral compositions of the present invention preferably at a concentration of about 0.5 to about 8.0% by weight. In liquid oral preparations, the pyrophosphate salts are incorporated at a concentration of about 0.1 to about 3% by weight.

Antibacterial agents may also be included in the oral compositions of the present invention. Especially useful are non-cationic antibacterial agents which are based on phenolic and bisphenolic compounds, halogenated diphenyl ether, halogenated salicylanilides and particularly fluro salicylanilides, benzoate esters and carbanilides. Examples of such compounds are 4-chlorophenol, 2,2'-trichloro-2-hydroxy-diphenyl ether (Triclosan), 3, 4'5 trichlorosalicylanilide, 5-n-octanoyl-3'-trifluoromethyl esters of p-hydroxybenzoic acid, especially methyl, ethyl, propyl, butyl and benzyl esters, 3,4,4'-trichlorocarbanilide and 3,3',4-trichlorocarbanilide. Triclosan and 5-n-octanoyl-3'-trifluromethyl salicylanilide in amounts ranging from 0.03% to 1% are preferred for use in the compositions of the present invention. A nonionic antimicrobial agent such as sesquiterpene alcohols such as merolidol and bisabolol are also useful in the present invention.

When antibacterial agents are included in the oral compositions of the present invention, an antibacterial enhancing agent may also be included in the oral composition. The use of antibacterial enhancing agents in combination with antibacterial agents such as Triclosan and halogenated salicylanilide in known to the art, as for example U.S. Pat. No. 5,188,821 and U.S. Pat. No. 5,192,531. Preferably, the antibacterial enhancing agent is a natural or synthetic anionic polymeric polycarboxylate having a molecular weight of about 1,000 to about 1,000,000, preferably about 30,000 to about 500,000. The synthetic anionic polymeric polycarboxylates are generally employed in the form of their free acids or preferably partially or more preferably fully neutralized water soluble alkali metal e.g., potassium and preferably sodium or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 500,000. These copolymers are available, for example, as Gantrez, e.g. AN 139 (M.W. 500,000), AN 119 (M.W. 250,000); and preferably S-97 Pharmaceutical Grade (M.W. 70,000), of GAF Corporation.

Polysiloxanes such as liquid silicone oils such as diphenyl or di ($C_1$–$C_4$) alkyl polysiloxanes and particularly dimethyl-polysiloxane, may also be employed in the practice of the present invention as an antibacterial enhancing agent.

The antibacterial enhancing agent is incorporated in the compositions of the present invention in weight amounts of about 0.05 to about 5%, and preferably about 0.1 to about 3%.

Any suitable flavoring or sweetening material may also be employed. Examples of suitable flavoring constituents are flavoring oils, e.g. oil of spearmint, peppermint, wintergreen, sassafras, clove, sage, eucalyptus, cinnamon, lemon, and orange, and methyl salicylate. Suitable sweetening agents include sucrose, lactose, maltose, xylitol, sodium cyclamate, perillartine, aspartyl phenyl alanine, methyl ester, saccharine and the like. Suitably, the flavor and sweetening agents may each or together comprise from about 0.1% to 5% more of the preparation.

Agents used to diminish teeth sensitivity such as strontium chloride, potassium nitrate and potassium citrate can also be included in the oral compositions of the present invention at concentrations of about 0.1% to about 10% by weight.

Various other materials may be incorporated in the oral compositions of this invention such as preservatives, such as sodium benzoate, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Tooth whitening agents may also be included in the oral compositions of the present invention. Especially useful are oxidizing agents such as, hydrogen peroxide, urea peroxide, peracetic acid, calcium peroxide, sodium perborate, sodium percarbonate or any other source that, in aqueous solutions, acts as an hydrogen peroxide source. The amount of active oxygen in such oral compositions can vary from 0.7% to 5% by weight and preferably about 0.5% to about 2% by weight.

The oral composition of the present invention may be prepared by suitably mixing the ingredients. In the preparation of the semi-solid or pasty composition such as a toothpaste, a thickener such as carboxymethyl cellulose or hydroxyethyl cellulose is dispersed with a humectant, water, salts such as tetrasodium pyrophosphate, sodium fluoride or sodium monofluorophosphate, and sweetener such as saccharin are then added and mixed. A polishing agent such as dicalcium phosphate dihydrate, purified sodium lauryl sulfoacetate and alkyl glycoside surfactants and flavor are then added. The ingredients are then mixed under vacuum for about 15–30 minutes. The resulting gel or paste is then tubed.

The following examples are further illustrative of the present invention, but it is understood that the invention is not limited thereto. All amounts and proportions referred to herein and in the appended claims are by weight unless otherwise indicated.

Example I

A series of toothpastes was prepared having the compositions listed in Table I, in which the surfactant system comprised 1.3% by weight of the composition.

TABLE I

| INGREDIENT | COMPOSITION A WEIGHT % | B | C |
|---|---|---|---|
| Dicalcium phosphate dihydrate | 48.00 | 48.00 | 43.00 |
| Glycerin | 22.22 | 22.22 | 22.22 |
| Sodium lauryl sulfoacetate (purified)* | 1.30 | 0.86 | 0.91 |
| $C_{12}$–$C_{16}$ alkyl glycoside** | — | 0.44 | 0.39 |
| Flavor | 0.95 | 0.95 | 0.95 |
| Sodium monofluorophosphate (MFP) | 0.76 | 0.76 | 0.76 |
| Na Carboxymethyl cellulose (NaCMC) | 0.50 | 0.50 | 0.50 |
| Hydroxyethyl Cellulose (HEC) | 0.50 | 0.50 | 0.50 |
| Tetrasodium pyrophosphate (TSPP) | 0.25 | 0.25 | 0.25 |
| Na Saccharin | 0.20 | 0.20 | 0.20 |
| Deionized water | q.s. | q.s. | q.s. |
| pH 6.6–7.2 | | | |

*Analysis of purified sodium lauryl sulfoacetate:

|  | wt % |
|---|---|
| dodecyl sodium sulfoacetate | 82–85 min. |
| sodium chloride | 7.5–8.0 max. |
| sodium sulfate | 7.5–8.0 max. |
| sodium sulfoacetate | <4 max |
| free alcohol | <0.6–0.8 max. |

**Analysis of alkyl glucoside (Planteran 1200 UP):

| Activity, % | 48–52 |
|---|---|
| Free alcohol, % | 0.4–0.8 |
| Average D.P. | 1.4 |
| pH, 10% sol. | 11.4–11.8 |

The composition was prepared by mixing glycerin together with NaCMC and HEC, then adding TSPP and Na Saccharin, following by deionized water. The mixture was placed in a double planetary vacuum mixer. Dicalcium phosphate dihydrate, MFP, flavor, purified sodium lauryl sulfoacetate and alkyl glycoside were added to the mixture, and the ingredients mixed under vacuum for about 15–20 minutes. Homogeneous pastes were obtained using compositions A–C which, when evaluated by a taste panel, were found to have a pleasant, nonbitter taste.

For purposes of comparison a second series of toothpaste compositions was prepared following the procedure of Example I except either Tween 60, a non-ionic polyoxyethylene (60) sorbitan monolaurate surfactant (composition D) or Pluronic F127 a nonionic polyethyleneoxide/polypropyleneoxide block copolymer was substituted for the alkyl glycoside (composition E) or SLS (composition F) was used as the sole surfactant. The composition of these comparative toothpaste compositions also containing 1.3% by weight of the specific surfactant system are recorded in Table II below.

TABLE II

| INGREDIENTS | COMPOSITION D WEIGHT % | E | F |
|---|---|---|---|
| Dicalcium phosphate dihydrate | 48.00 | 48.00 | 48.00 |
| Glycerin | 22.22 | 22.22 | 22.22 |
| Sodium lauryl sulfate | — | — | 1.30 |
| Sodium lauryl sulfoacetate (purified)* (SLSA) | 0.78 | 0.52 | — |
| Tween 60 | 0.52 | — | — |
| Pluronic F127 | — | 0.78 | — |
| Flavor | 0.95 | 0.95 | 0.95 |
| Sodium monofluorophosphate (MFP) | 0.76 | 0.76 | 0.76 |
| Carboxymethyl cellulose (CMC) | 0.50 | 0.50 | 0.50 |
| Hydroxyethyl Cellulose (HEC) | 0.50 | 0.50 | 0.50 |
| Tetrasodium pyrophosphate (TSPP) | 0.25 | 0.25 | 0.25 |
| Na Saccharin | 0.20 | 0.20 | 0.20 |
| Deionized water | q.s. | q.s. | q.s. |

Toothpastes D and E when evaluated by a taste panel were found to have an unpleasant bitter taste. Toothpaste F was found to have an acceptable taste.

To assess the stability of the toothpastes A–F to viscosity change, the compositions were stored at 23° C. for up to 12 weeks. The Brookfield viscosities of composition A–F were measured periodically as a function of time using Brookfield RVT, Spindle E at 5 rpm. A viscosity measurement above 50 Brookfield Units in this test indicates that the product is unacceptable for consumer use as the product at this viscosity level, is extremely viscous and not readily extrudable from a tube.

The results of the storage stability tests are recorded in Table III below.

TABLE III

| | | VISCOSITY CHANGE OVER TIME | | | |
|---|---|---|---|---|---|
| | | | Time Elapsed | | |
| Toothpaste | Surfactant System | Initial | 3 wks | 6 wks | 12 wks |
| | | Viscosity (Brookfield Units) | | | |
| A | SLSA | 18 | >100 | >100 | 98.5 |
| B | SLSA/AG (2:1) | 27 | 33 | 36 | 41 |
| C | SLSA/AG (7:3) | 27 | 35 | 43.5 | 41 |
| D | SLSA/TWEEN 60 (3:2) | 24 | 27.5 | 31.5 | 29.0 |
| E | SLSA/F-127 (2:3) | 43.5 | 45 | 45.5 | 52.1 |
| F | SLS | 26 | 36 | 36 | 41 |

The results recorded in Table III indicate that Toothpaste A in which purified sodium lauryl sulfoacetate was the sole surfactant underwent a viscosity increase to greater than 100 Brookfield Units after 3 weeks storage, which viscosity level rendered the toothpaste unacceptable for consumer use, whereas toothpastes formulated with a purified sodium lauryl sulfoacetate(SLSA)/alkyl glycoside (AG) surfactant system of the present invention (Toothpastes B and C) were comparable to toothpastes formulated with the conventional surfactant sodium lauryl sulfate (Toothpaste F). Toothpastes formulated with sodium lauryl sulfoacetate and a nonionic co-surfactant such as Tween 60 or Pluronic F-127 (toothpastes D and E) also exhibited acceptable viscosity stability but as previously noted the organoleptic properties of these toothpastes were unacceptable for consumer use.

EXAMPLE II

To assess the foaming properties of the toothpastes of the present invention (Toothpastes B and C of Example I), an artificial saliva solution was prepared following the procedure disclosed in Tavss et al J. Pharm. Sci, 1984, 73(g), 1148-52 having the composition shown below

| COMPOSITION OF ARTIFICIAL SALIVA | |
|---|---|
| INGREDIENT | CONCENTRATION (g/l) |
| $CaCl_2.2H_2O$ | 0.228 |
| $MgCl_2.6H_2O$ | 0.061 |
| NaCl | 1.017 |
| $K_2CO_3.15H_2O$ | 0.603 |
| $NaH_2PO_4.H_2O$ | 0.204 |
| $Na_2HPO_4.7H_2O$ | 0.273 |
| Water | q.s. |
| Conc. HCl | sufficient to achieve pH 6.9 |

To the artificial saliva was added 16% by weight dicalcium phosphate dihydrate and 0.3% by weight flavoring agent along with 0.4 wt % of a surfactant system consisting of purified sodium lauryl sulfoacetate and alkyl polyglycoside at varying weight ratios, which are shown in Table IV. The concentrations of the resulting test solution correspond to a 1:2 dilution of toothpaste in saliva normally associated with toothpaste in the oral cavity.

In performing the foam test, fifteen ml of the test solution were transferred to a 50 ml sterile centrifuge tube. Six replicates were placed in a 37° C. water bath for approximately 15 minutes. The centrifuge tubes were clamped on to a Burrell Wrist-Action Shaker and were shaken an average of 50 times over a 10 second period. The tubes were displaced over 7.0 cm in each cycle. Upper and lower foam levels were recorded on the tubes between 5 and 20 seconds after shaking. The difference in the levels provided a "foam volume" value in milliliters. Increasing foam values correlate to increasing foamability perceived by consumers using the toothpaste.

A 0.98 correlation was found to exist between the foam test results using diluted toothpaste and the foamability rated by a human test panel brushing with undiluted toothpaste. The foam volume of the test solutions is recorded in Table IV below (Run Nos. 1-3).

For purposes of comparison, the procedure of the Example was repeated except a solution was prepared wherein purified sodium lauryl sulfoacetate was the sole surfactant and this solution was also tested for foamability. The foam values of this comparative solution designated "C" are also recorded in Table IV.

TABLE IV

| Toothpaste Foamability | | | |
|---|---|---|---|
| Run No. | Surfactant System | Ratio SLSA/AG | Foam Volume (ml) |
| 1 | SLSA/AG | (9:1) | 22 |
| 2 | SLSA/AG | (4:1) | 23.5 |
| 3 | SLSA/AG | (7:3) | 21 |
| C | SLSA | | 21 |

The data in Table IV show that, the oral compositions containing the purified sodium lauryl sulfoacetate/alkyl glycoside surfactant systems exhibited foaming levels equal to or better than the purified sodium lauryl sulfoacetate alone (Run No. C).

EXAMPLE III

The irritancy of the purified sodium lauryl sulfoacetate/alkyl glycoside surfactant system used to prepare the toothpaste compositions of the present invention was evaluated in accordance with the test procedure disclosed in an article entitled "Predicting Surfactant Irritation from the Swelling Response of a Collagen Film," J. Soc. Cosmet, Chem. 37, 199-210 (July/August, 1986). In this test, the swelling (tritriated water uptake) of a collagen film substrate correlates with the irritation of anionic surfactants and products based on these ingredients. Swelling response is concentration dependent and higher substrate swelling indicates greater irritation potential. The results of this in vitro test have been found to correlate with findings from established in vitro and in vivo laboratory and clinical assessments.

In performing the irritancy test, collagen film supplied by Colla-Tec Inc., Plainsboro, N.J., was prepared from bovine deep flexor tendon and cut into 1.27×1.27 cm (0.5× 0.5 inch) squares, approximately 10 mg by weight. Each square was placed in a 20-ml screw cap vial and treated with 10 ml solution containing 1% a mixture of purified sodium lauryl sulfoacetate (SLSA) in combination with the alkyl glucoside (AG) Planteran 1200 and enough tritiated ($^3H_2O$) water to give $1 \times 10^5$ dpm/ml.

The above procedure was then repeated with the exception that the film squares were exposed to a 10 ml solution obtained by diluting toothpastes of Example I (1:1 dilution) with water and then centrifuging to obtain a supernatant liquid that was used as the test solution.

The film squares were removed from all the solutions, and each rinsed in a liter of deionized water for about 5 seconds to remove any adhering tritiated water, and thereafter placed in a liquid scintillation vial.

The films exposed to the 1% surfactant solutions (hereinafter "surfactant solution") and the diluted toothpaste solutions (hereinafter "toothpaste solutions") were digested in the vials with 1 ml 2N NaOH and dissolved in Ecolume (ICN Biomedicals, Inc.) scintillation cocktail, acidified with 0.25 ml concentrated perchloric acid, and analyzed for radioactivity using a Beckman LS06800 scintillation spectrometer. The swelling was defined as microliters tritiated water taken up per milligram dry collagen (ul/mg). The results are recorded in Table V below.

For purposes of comparison, the irritancy test was repeated with the exception that the irritancy of a surfactant system consisting solely of (sodium lauryl sulfate SLS) at the same concentration as the purified sodium lauryl sulfoacetate/alkyl glucoside system was also determined. The results of this comparative test is also recorded in Table V below. An irritancy test using water as a control was also run.

TABLE V

| Test No. | Surfactant System | Surfactant Irritancy | | Irritancy Collagen Swelling ul/mg | |
|---|---|---|---|---|---|
| | | Surfactant Concentration (Wt %) | | | |
| | | Surfact. Soln | Toothpaste Soln | Surfact. Soln | Toothpaste Soln |
| 1. | SLSA/AG | 0.455/0.195 | 0.455/0.195 | 7.52 ± 0.22 | 5.40 ± 0.07 |
| 2. | SLS | 0.65 | 0.65 | 16.19 ± 0.17 | 6.31 ± 0.25 |
| 3. | Water | — | — | 4.30 ± 0.28 | 4.30 ± 0.28 |

The results recorded in Table V indicate that purified sodium lauryl sulfoacetate/AG System was substantially less irritating than sodium lauryl sulfate present at the same concentration in the test solutions.

What is claimed is:

1. A substantially non-irritating oral composition of acceptable taste having improved stability to viscosity change on storage, the composition containing a surfactant system comprised of an effective amount of a sodium lauryl sulfoacetate surfactant purified to contain about 18% or less by weight impurities and an alkyl glycoside having the formula RO $(C_6H_{10}O_5)_xH$, wherein R is an aliphatic residue of a $C_{12}$ to $C_{22}$ fatty alcohol and x is an integer from 1 to 20.

2. The composition of claim 1 wherein the alkyl glycoside is characterized by the R being an aliphatic residue of a $C_{12}$ to $C_{16}$ fatty alcohol and x is an integer from 1.2 to 2.0.

3. The composition of claim 2 wherein x in the formula is 1.4.

4. The composition of claim 1 wherein the purified sodium lauryl sulfoacetate surfactant has the following analysis:

| | wt % range |
|---|---|
| dodecyl sodium sulfoacetate | 82.0–85.0 min |
| sodium chloride | 7.5–8.0 max |
| sodium sulfate | 7.5–8.0 max |
| sodium sulfoacetate | <4 max |
| free alcohol | <0.6–0.8 max |

5. The composition of claim 1 wherein the purified sodium lauryl sulfoacetate is present in the oral composition at a concentration of about 0.1% to about 3.0% by weight and the alkyl glycoside is present in the oral composition at a concentration of 0.1% to 2.0%.

6. The composition of claim 3 wherein the weight ratio of sulfoacetate to glycoside is from 10:1 to 1:5.

* * * * *